US009228796B2

(12) United States Patent
Adcock, Jr. et al.

(10) Patent No.: US 9,228,796 B2
(45) Date of Patent: Jan. 5, 2016

(54) UTILITY FOREGRIPS FOR USE WITH FIREARMS, AND RELATED METHODS

(71) Applicant: SWITCH GRIP LLC, Massillon, OH (US)

(72) Inventors: Torrance L. Adcock, Jr., Bethesda, MD (US); Michael Christopher Rice, Massillon, OH (US)

(73) Assignee: Switch Grip LLC, Massillon, OH (US)

( * ) Notice: Subject to any disclaimer, the term of this patent is extended or adjusted under 35 U.S.C. 154(b) by 142 days.

(21) Appl. No.: 14/143,987

(22) Filed: Dec. 30, 2013

(65) Prior Publication Data

US 2014/0215884 A1    Aug. 7, 2014

Related U.S. Application Data

(60) Provisional application No. 61/747,705, filed on Dec. 31, 2012.

(51) Int. Cl.
| | |
|---|---|
| *F41C 23/16* | (2006.01) |
| *F41B 13/00* | (2006.01) |
| *F41B 13/08* | (2006.01) |
| *F41C 23/22* | (2006.01) |
| *F41C 27/16* | (2006.01) |
| *F41G 11/00* | (2006.01) |

(52) U.S. Cl.
CPC .................. *F41C 23/16* (2013.01); *F41B 13/00* (2013.01); *F41B 13/08* (2013.01); *F41C 23/22* (2013.01); *F41C 27/16* (2013.01); *F41G 11/003* (2013.01); *Y10T 29/49* (2015.01); *Y10T 29/49817* (2015.01)

(58) Field of Classification Search
CPC ............. F41C 9/02; F41C 23/16; F41C 23/22

USPC .......... 42/53, 1.09, 86, 72, 72.01, 106, 90, 94
See application file for complete search history.

(56) References Cited

U.S. PATENT DOCUMENTS

| | | | |
|---|---|---|---|
| 545,528 | A | 9/1895 | Paul |
| 1,023,741 | A | 4/1912 | Kreith |
| 1,231,058 | A | 6/1917 | Pansa |

(Continued)

FOREIGN PATENT DOCUMENTS

| | | | | |
|---|---|---|---|---|
| CA | 2579060 | A1 * | 3/2006 | ............. F41C 23/16 |
| CN | 1195105 | A | 10/1998 | |

(Continued)

OTHER PUBLICATIONS

International Search Report and Written Opinion for PCT Application No. PCT/US2013/078504, mailed May 1, 2014.
Http://www.m34tactical.com/raptor.html, "Raptor Dagger", printed Jun. 12, 2013, website is undated but inventor believes the website is older than May 14, 2013.

(Continued)

*Primary Examiner* — Benjamin P Lee
(74) *Attorney, Agent, or Firm* — Sand & Sebolt; Howard L. Wernow (57) ABSTRACT

A foregrip for a firearm may comprise a mounting device configured to attach to a mounting rail of a firearm and a grip body. The grip body may include a top portion configured to be removably attached to the mounting device and a lateral side portion configured to be gripped by the hand of a person using a firearm. A cavity may be disposed within the grip body, and a blade may be disposed at least partially within the cavity, wherein the blade is movable between a refracted position and a deployed position relative to the grip body.

19 Claims, 7 Drawing Sheets

(56) References Cited

U.S. PATENT DOCUMENTS

| | | | |
|---|---|---|---|
| 2,805,507 A | 9/1957 | Buquor | |
| 5,594,967 A | 1/1997 | Morton et al. | |
| 5,924,233 A * | 7/1999 | Strobel | 42/72 |
| 6,209,250 B1 * | 4/2001 | Mills | 42/53 |
| 6,389,729 B2 * | 5/2002 | Rauch et al. | 42/72 |
| 8,196,328 B2 * | 6/2012 | Simpkins | 42/73 |
| 8,650,791 B2 * | 2/2014 | Williams | 42/72 |
| 8,661,723 B2 * | 3/2014 | Emde et al. | 42/71.02 |
| 8,984,789 B2 * | 3/2015 | Adcock, Jr. | 42/72 |
| 2006/0162224 A1 | 7/2006 | Connal | |
| 2007/0271832 A1 | 11/2007 | Griffin | |
| 2009/0133309 A1 | 5/2009 | Cahill | |
| 2010/0132239 A1 | 6/2010 | Moody et al. | |
| 2011/0173862 A1 * | 7/2011 | Williams | 42/72 |
| 2014/0338245 A1 | 11/2014 | Lanasa et al. | |

FOREIGN PATENT DOCUMENTS

| | | | | |
|---|---|---|---|---|
| GB | 14863 A | * | 9/1916 | |
| GB | 14863D | * | 9/1916 | F41C 27/16 |
| GB | 571902 A | * | 9/1945 | F41C 27/16 |

OTHER PUBLICATIONS

Http://www.flickr.com/photos/48470964@N002/4442555408, pimpmygun.doctornoob.com, printed Jun. 12, 2013, website is undated but inventor believes the website is older than May 14, 2013 (unable to print original website as site no longer exists).

http://flickr.com/photos/48470964@n02/4444306510/in/ photostream, pimpmygun.doctornoob.com, printed Jun. 12, 2013, website is undated but inventor believes the website is older than May 14, 2013 (unable to print original website as site no longer exists).

www.everydaynodaysoff.com/2012/07/05/bringing-a-knight-to-a-gunfight/, "Bringing a Knight to a Gunfight", author unknown, printed Jun. 12, 2013, website is undated but inventor believes the website is older than May 14, 2013.

www.amazon.com, "Kubaton 4 In. Black Keychain with Concealed Knife", printed Jun. 12, 2013, website is undated but inventor believes the website is older than May 14, 2013.

www.ar15.com, "Samson Knives for the AR15 Grip with Pics", Printed Jun. 12, 2013, website is undated but inventor believes the website is older than May 14, 2013.

* cited by examiner

UTILITY FOREGRIPS FOR USE WITH FIREARMS, AND RELATED METHODS

CROSS-REFERENCE TO RELATED APPLICATION

This application claims the benefit of U.S. Provisional Patent Application Ser. No. 61/747,705, filed Dec. 31, 2012, the disclosure of which is hereby incorporated herein in its entirety by this reference.

TECHNICAL FIELD

Embodiments of the present disclosure relate to firearms, and in particular, to a foregrip removably attachable to the forward part of a rifle, and to methods of making and using such a foregrip.

BACKGROUND

The Armalite Rifle (AR) platform has been the standard battle rifle platform of the United States for the past fifty years. Introduced in the 1960s as a replacement for the M-14 rifle, M-16s were deployed in Vietnam as the military's new standard battle rifle. The M-16 was originally known as the AR-15, the designation originating from the Armalite Company that produced the first M-16s.

In the intervening years, the AR platform evolved to more sophisticated configurations and capabilities. One major innovation was the introduction of the Picatinny rail system adopted as a standardized mounting system that allows accessories from multiple vendors to be mounted on the battle rifle and interchangeable from one weapon to another.

The Picatinny rail, alternatively known as the U.S. MIL-STD-1913 rail, NATO STANAG 2324 rail, or simply "Tactical Rail," is a bracket used on firearms in order to provide a standardized mounting platform. The Picatinny rail is a dovetail or T-shaped mount with transverse grooves that prevent the mounting accessory from moving back and forth due to recoil. The rail comprises a series of ridges with a T-shaped cross-section interspersed with flat "spacing slots." Accessories are mounted either by sliding them on from one end to the other by means of a mount that is clamped to the rail with bolts, thumbscrews or levers, or onto the slots between raised sections.

With the advent of the Picatinny rail system, manufacturers began producing various accessories to aid soldiers in the field with a wide array of products ranging from multiple telescopic sights, range-finding devices, red-dot aiming devices, laser aiming devices, rail-mounted flashlights, alternate sights, and bi-pods, all of which represent the majority of categories of accessories available for mounting on the Picatinny rails. Vertical foregrips and other accessories mounted at the six o'clock position on shoulder-fired weapons have become known in military, law enforcement and civilian arenas.

A vertical foregrip is designed to attach to a firearm for the forward hand (or "offhand"). Such vertical foregrips aid in the maneuverability of the firearm, since the natural angle of a person's outstretched hand is more oriented to grasping objects at a vertical angle, rather than a horizontal one perpendicular to the body. Prior art foregrips attachable to rifles provide some levels of utilization but are less functional in design. Most foregrips of this type are constructed whereby the interior of the foregrip is a hollow cavity for storing "small parts." Other uses comprise installing batteries inside the foregrip cavity to power Picatinny rail-mounted flashlights, or where the foregrip and flashlight are an integral unit and the batteries again are contained within the foregrip cavity. Some prior art grips provide the option of allowing the foregrip to be positioned at various angles.

BRIEF SUMMARY

In one embodiment, a foregrip for a firearm may comprise a mounting device configured to attach to a mounting rail of a firearm and a grip body. The grip body may include a top portion configured to be removably attached to the mounting device and a lateral side portion configured to be gripped by the hand of a person using a firearm. A cavity may be disposed within the grip body, and a blade may be disposed at least partially within the cavity, wherein the blade is movable between a refracted position and a deployed position relative to the grip body.

In another embodiment, a method of manufacturing a foregrip for a firearm may comprise forming a mounting device configured to mount to a mounting rail of a firearm, forming a grip body including a top portion configured to removably attach to the mounting device and a lateral side portion configured to be gripped by a firearm user, and providing a blade disposed within a cavity of the grip body. The blade may be moveable between a refracted and a deployed position.

In yet another embodiment, a method of using a firearm may comprise coupling a mounting device to a rail of the firearm, removably attaching a foregrip including a utility device therein to the mounting device, the foregrip including a grip body having a top portion configured for attachment to the mounting device, a lateral side portion configured to be gripped by a firearm user, and a blade disposed within a cavity of the grip body, the blade being moveable between a refracted position and a deployed position relative to the grip body, detaching the foregrip from the mounting device and the firearm, and moving the blade from the refracted position to the deployed position.

In yet another embodiment, a foregrip for a firearm may comprise a mounting device configured to attach to a mounting rail of a firearm, a grip body with a top portion configured to be removably attached to the mounting device and a lateral side portion configured to be gripped by the hand of a person using a firearm, a cavity disposed within the grip body, and a utility device disposed at least partially within the cavity.

Applicant has devised several accessories configured for the Picatinny rail system that are not only unique in design, but are highly functional as well. The functionality is in keeping with the demands of soldiers, police and civilian shooters who require ease of use, practicality, and ruggedness from the equipment they must rely on when in the field and under harsh conditions. Additional variations on the present invention incorporate multi-functionality within these devices. The differences lie in the use of the functional devices incorporated into vertical foregrips making them not only unique but practical as well, all of which feature requested "one-handed" operation.

To accomplish this, the present invention provides a vertical foregrip (VFG) in several configurations. Each configuration provides end-users with a secure grip for holding the weapon in a firing position while also providing additional functionality in the form of tools and other functional devices that are incorporated into the grip itself for use while in the field.

The invention grip is not merely used to store articles, but is an integral part of the tool itself.

For purposes of this application, Applicant provides six configurations as follows:

Version #1 (VFG-1) provides a vertical foregrip with an integral sliding blade.

Version #2 (VFG-2) provides a vertical foregrip with an integral razor (or box-cutter).

Version #3 (VFG-3) provides a vertical foregrip with an integral multi-tool configuration (similar to a Swiss army knife).

Version #4 (VFG-4) provides a vertical foregrip with an integral flashlight).

Version #5 (VFG-5) provides a vertical foregrip that may be rotated to a horizontal position; the ability to re-position the vertical foregrip (VFG) affects the angle at which the weapon is held while in the firing position thus making it easier for the operator/shooter to position the weapon when firing.

Version #6 (VFG-6) provides a vertical foregrip with an integral folding knife blade that employs a "liner-lock" mechanism to keep the blade from collapsing on the user's hand.

These, together with other objects of the invention, along with various features of novelty that characterize the invention, are pointed out with particularity in the drawings and specification annexed hereto and forming a part of this disclosure. For a better understanding of the invention, its operating advantages and the specific objects attained by and that engage the flanges it uses, reference should be made to the accompanying drawings and descriptive matter in which there is illustrated a preferred embodiment of the invention.

BRIEF DESCRIPTION OF THE DRAWINGS

While the specification concludes with claims particularly pointing out and distinctly claiming what are regarded as embodiments of the present invention, advantages of the embodiments may be more readily ascertained from the following description of certain example embodiments when read in conjunction with the accompanying drawings in which:

DETAILED DESCRIPTION

The illustrations presented herein are not meant to be actual views of any particular vertical foregrip or components thereof, but are merely idealized representations that are employed to describe embodiments of the present disclosure. Additionally, elements common between figures may retain the same numerical designation.

Referring to the drawings in detail wherein like elements are indicated by like numerals, there are the five versions of the VFG as briefly described above. VFG-1 (FIGS. 2-4, 12, and 13) provides a vertical foregrip with an integral sliding blade. VFG-2 (FIG. 5) provides a vertical foregrip with an integral razor. VFG-3 (FIG. 6) provides a vertical foregrip with an integral multi-tool configuration. VFG-4 (FIG. 7) provides a vertical foregrip with an integral flashlight. VFG-5 (FIG. 8) provides a vertical foregrip that may be rotated to a horizontal position. VFG-6 (FIGS. 9-11) provides a vertical foregrip with a folding blade including a liner-lock mechanism.

Figure 1:
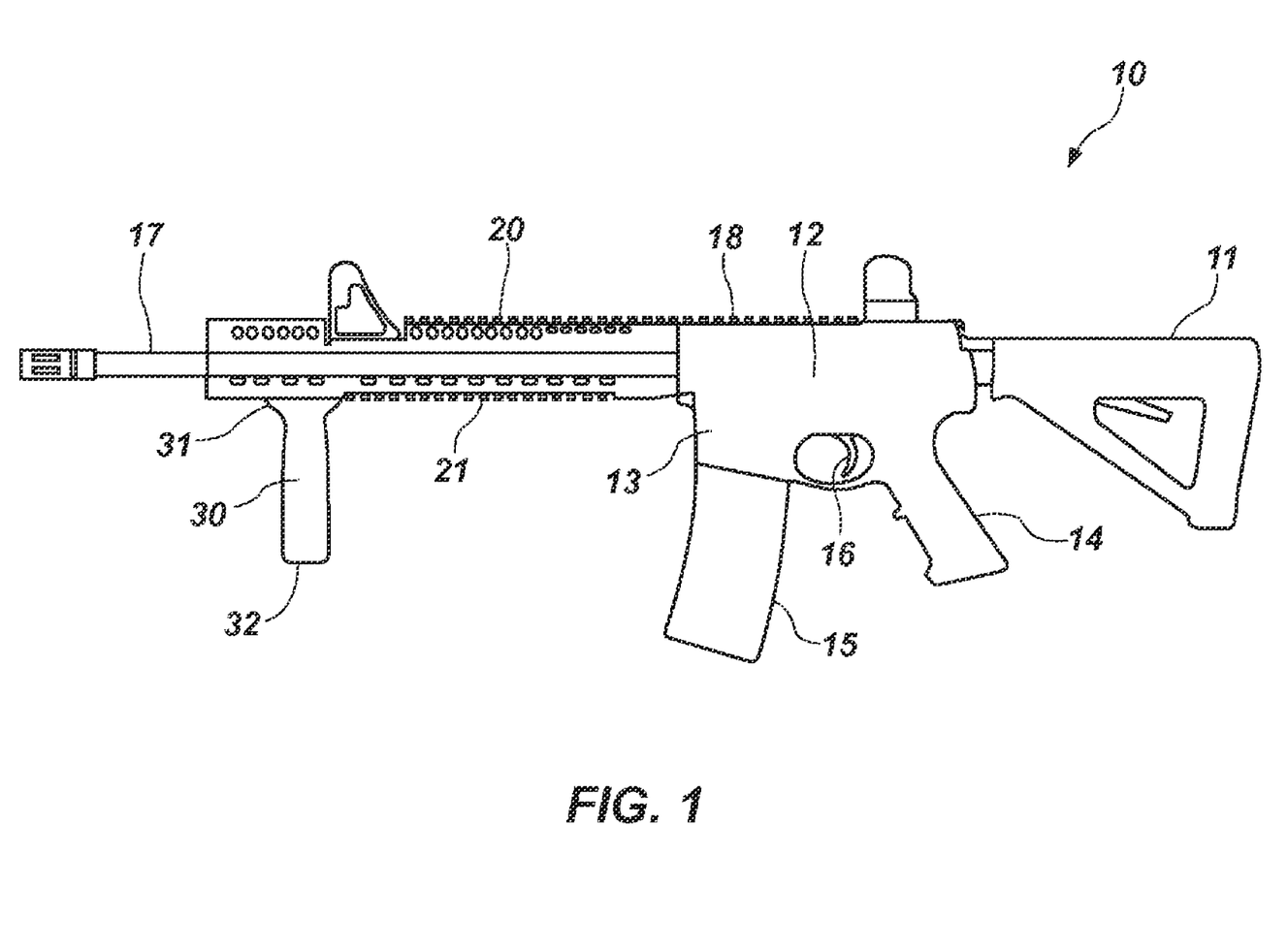
FIG. 1 is side view of an M-16 battle rifle with vertical foregrip.

FIG. 1 illustrates a conventional combat firearm 10, i.e., a U.S. M-16. The firearm 10 has a stock 11 forming the firearm rearward portion. The stock 11 terminates forwardly in a lower receiver 13 from which a pistol grip 14 downwardly and rearwardly protrudes. A magazine 15 protrudes downwardly and forwardly from the lower receiver 13. A trigger 16 protrudes downwardly from the lower receiver 13 between the pistol grip 14 and magazine 15. A rifle barrel 17 extends forwardly from an upper receiver 12 attached to the lower receiver 13 and defines the forward portion of the firearm. The longitudinal axis of the firearm 10 is defined by the stock 11, upper receiver 12, and barrel 17. A Picatinny rail assembly 20 extends from an upper receiver top 18 forward about a portion of the barrel 17, including rails 21 along the barrel's twelve, three, six and nine o'clock positions.

Figure 2:
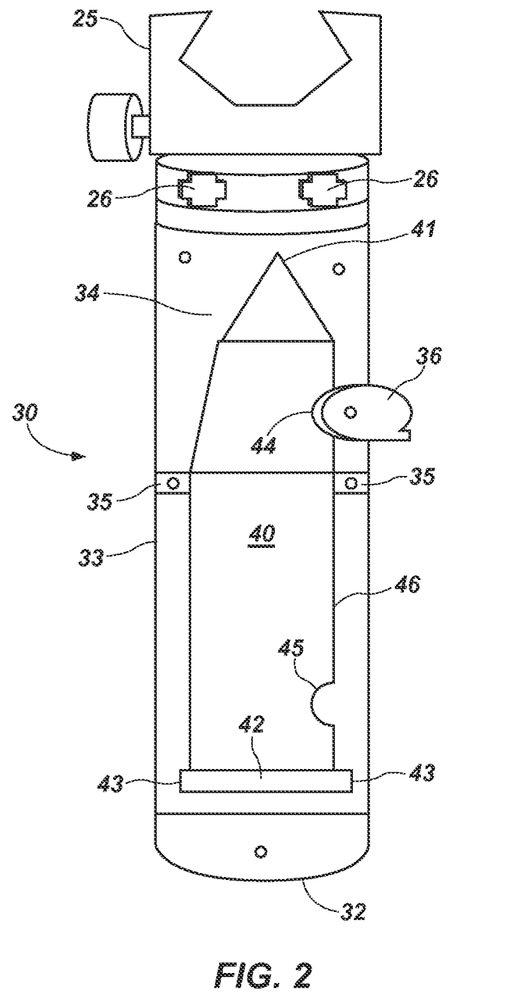
FIG. 2 is a diagrammed view of a vertical foregrip with integral sliding blade attached to a rail mounting device.
Figure 3:
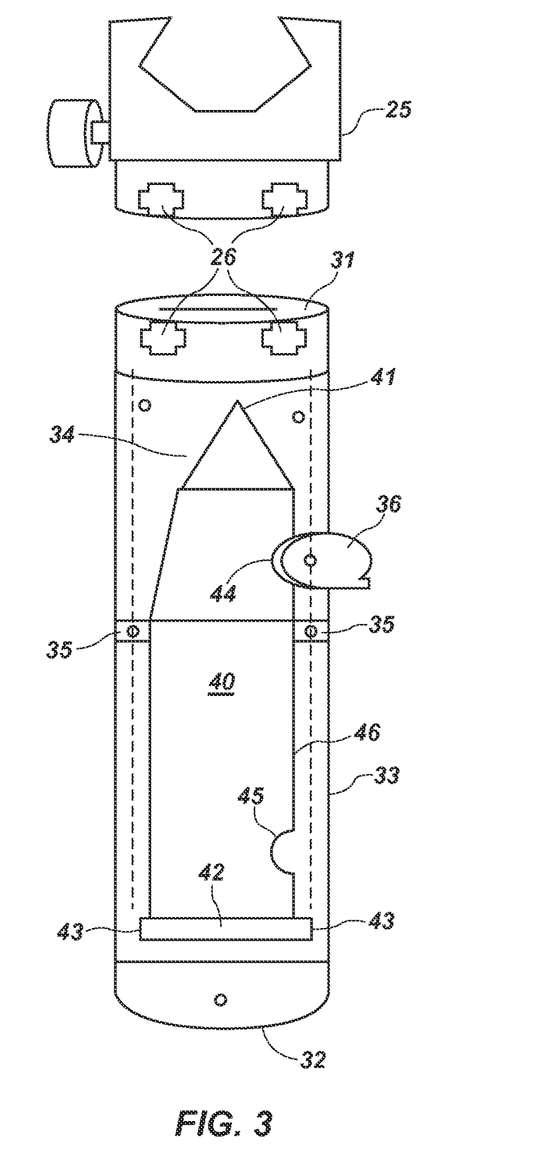
FIG. 3 is a diagrammed view of the vertical foregrip with blade fully inserted and separated from the mounting device.
Figure 4:
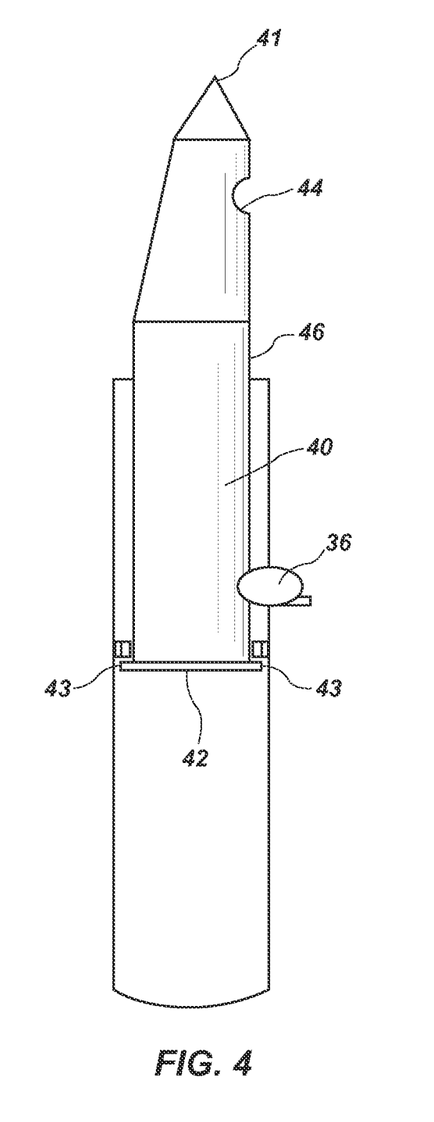
FIG. 4 is a diagrammed view of the vertical foregrip with blade deployed.

Referring to FIGS. 2-4, the VFG-1 (a vertical foregrip 30 with an integral sliding blade) may be attached to the Picatinny rail system rail 21 at the six o'clock position to provide shooters with a firm grip of the weapon to help position the rifle securely in the "pocket" of the shoulder as a solid platform from which to shoot the weapon and engage threats. The forward grip 30 may be hollow and may include a top 31, bottom 32, and sides 33 extending from bottom to top, and the top 31, bottom 32, and sides 33 may define a grip interior 34. The grip top 31 may be removably connected to a rail mounting device 25 by locking lugs, threads or similar complementary interlocking features 26 that removably attach the grip top 31 to the rail mounting device 25. The rail mounting device 25 may be adapted to connect to a Picatinny rail 21. The grip interior 34 may contain an elongated knife blade 40 having a distal end 41 and a proximal end 42. The knife blade distal end 41 typically will terminate in a point.

The integral knife blade 40 and grip 30 mounting device 25 may attach to the Picatinny rail 21 via the mounting device 25, which may be a circular, threaded component to which the top 31 of the foregrip itself may be attached. Attachment may be achieved by abutting the grip 30 against the mounting device (e.g., by inserting the top 31 of the foregrip into the mounting device 25), pressing upward to engage complementary interlocking features 26 such as special threads or lugs, and rotating the foregrip to lock the lugs into place to the mounting device. This action is similar to how the cap for some popular water bottles is attached to the bottle. As the cap is twisted it unlocks from the special internal threads, then the cap is separated from the bottle. To reattach the cap, the cap is pressed down onto the bottle to engage the special threads and twisted to lock the cap to the bottle. In similar fashion, the VFG threads may require that the foregrip be inserted in a vertical manner then twisted to engage the locking threads/lugs, thus securing the foregrip to the weapon.

The complementary interlocking features 26 may be engaged with one another to attach the grip 30 to the mounting device 25, and may be disengaged from one another to remove the grip 30 from the mounting device 25. For example, the complementary interlocking features 26 may include protrusions disposed on the top 31 of the grip 30 configured to engage complementary recesses in the mounting device 25 as the grip top 31 is inserted into the mounting device 25 and rotated. Attaching the grip 30 to the mounting device 25 may require less than a full turn (i.e., a 360° (three hundred sixty degree) turn) to engage the attachment features 26. In some embodiments, it may be required to turn the grip 90° (ninety degrees) or less to engage the attachment features 26. In some embodiments, it may be required to turn the grip 45° (forty-five degrees) or less to engage the attachment features 26. Similarly, removal of the grip 30 from the mounting device 25 may be accomplished by a turn of less than 90° (ninety degrees) or a turn of less than 45° (forty-five) degrees. The amount of rotation required to remove the grip 30 from the mounting device 25 may be chosen to enable the grip 30 to be removed from the mounting device 25 conveniently and quickly. Rotation of the grip 30 may be generally about a longitudinal axis thereof.

Additionally, the grip 30 may be constructed in two halves and secured by threaded screws or pins. The two halves may be machined or milled on the interior face to form a cavity 34 to accept the sliding knife blade 40 that resides on the foregrip interior 34. The channel for the knife blade 40 may include two "stops" or blocks 35 machined into the surface just below the locking mechanism 36 that engage lateral flanges 43 on the knife blade proximal end 42 to prevent the blade 40 from sliding completely out of the foregrip interior 34.

The grip 30 may include a locking mechanism 36 comprised of a thumb-activated toggle switch-type component that may perform several functions. (1) Starting with the blade 40 refracted within the foregrip 30, the toggle switch 36 may be pressed or rolled forward (or backward) to disengage from a top notch 44 machined into the blade 40 itself, thus freeing the blade 40 to slide out of the foregrip 30. Owing to different construction approaches, the toggle switch 36 can be made alternately to release the blade 40 upon pressing forward on the toggle switch 36 or pulling back on the toggle switch 36, and also can use springs to re-set the position of the toggle switch 36 with each action. (2) After activating the toggle switch 36, releasing or deploying the blade 40 requires that the foregrip 30 be given a quick flick of the wrist (or pointed downward to allow gravity to deploy the blade 40) so the blade 40 slides out the top 31 of the foregrip 30. The toggle switch 36 may be activated to engage a second lower notch 45 on the blade 40 thus locking the blade 40 in a deployed position. (3) To retract the blade 40, the toggle switch 36 may again be activated to release from the lower blade notch 45, and the blade 40/foregrip 30 may be held in an upright position permitting gravity to return the blade 40 to a refracted position and the toggle switch 36 is again re-set into the top notch 44 to retain the blade 40 within the foregrip interior 34.

The sliding knife blade 40 may include several features to make it functional with the foregrip 30. A spine or back edge (non-cutting surface) 46 may include two half-moon indentations 44, 45 milled into the blade 40 at a specified distance apart to properly engage the toggle switch 36 and position the knife blade 40 in the correct positions, whether deployed or refracted. The proximal end 42 of the blade may include two slightly protruding flanges 43 that engage the "stops" 35 within the foregrip interior 34 to prevent the blade 40 from sliding completely out of the foregrip 30.

The body of the foregrip 30 that holds the knife blade 40 may be manufactured in such a manner that the toggle switch 36 falls naturally under the thumb as the hand grasps the foregrip 30 and activates the release mechanism. Also, the body of the foregrip 30 may be manufactured in two halves and joined by removable screws or pins so the blade 40 can be serviced for cleaning, re-sharpening, or replacement. Lastly, the top 31 of the foregrip may be manufactured in such a manner as to engage with the Picatinny rail mounting device 25, such that when the foregrip 30 is rotated, the special threads or lugs on the interior of the grip disengage and the foregrip 30 is pulled free of the Picatinny mounting device 25.

In use, the end-user (soldier, police officer, or civilian shooters) grasps the grip 14 of the rifle 10 with the firing hand and the vertical foregrip 30 with the free hand. Using the vertical foregrip 30, shooters pull the rifle 10 tight against their shoulder to provide a stable platform for aiming and shooting the weapon 10.

When shooters need to deploy the knife 40, as they already are grasping the body of the foregrip 30, they push the grip 30 tighter into the mounting device 25 and twist the foregrip 30 to release the locking threads/lugs from the mounting device 25 then pull down on the foregrip 30 to free it from the mounting device 25. With the thumb of the hand grasping the foregrip 30, shooters activate the locking toggle switch 36 to release the blade 40 within the foregrip 30. With a sharp flick of the wrist, or by pointing the foregrip 30 downward, the blade 40 slides out of the body of the foregrip 30 with the grip 30 acting as a blade handle. Activating the locking toggle switch 36 again locks the blade 40 with distal end 41 protruding in the deployed position. Shooters can then use the blade 40 as needed.

Besides the uniqueness and functionality of the combined foregrip and knife, shooters can use this device in a one-handed operation without the need to release the grip on their battle rifle. Cited time and again, soldiers prefer AR-mounted accessories to be a one-handed operation wherever possible. The present invention knife satisfies that request.

The present disclosure provides more than one function by offering soldiers or shooters both a functioning foregrip and a field knife, which, as every soldier knows, there is always a need for edged-tools when in the field. Having a readily available blade makes their job much easier, thus providing multi-functional devices to aid soldiers and other shooters as well.

Figure 5:
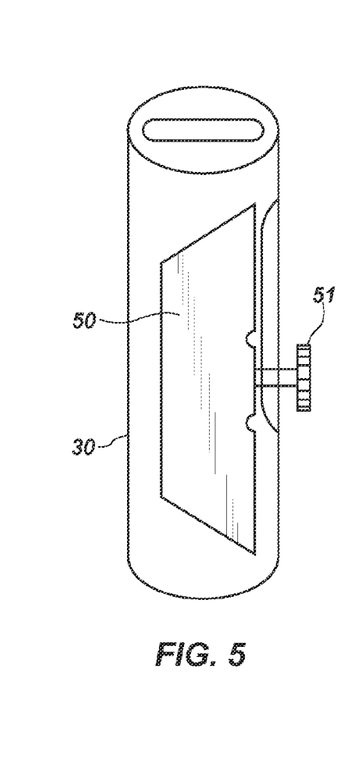
FIG. 5 is a diagrammed view of the vertical foregrip with box-cutter enclosed.

The VFG-2 (vertical foregrip with an integral razor or box-cutter blade; FIG. 5) may be similar in design to the VFG-1 wherein the foregrip top 31 attaches via the mounting device 25 to the Picatinny mounting rail 21. This embodiment of the vertical foregrip 30 may include an internal box cutter-type configuration 50 whereby industrial razor blades (drywall razors) can be installed in the foregrip for use when an edged-tool is required. This alternative design recognizes that in many jurisdictions within the United States, "gravity" knives are considered illegal. And many other jurisdictions limit the acquisition and use of switchblades and "gravity" type knives to active-duty military and police. This omits usage by a large section of the civilian population of the VFG-1 knife. To meet the needs of civilian users and to provide soldiers/police officers with alternatives to the VFG-1 knife configuration, applicant provides a box cutter design.

In place of the locking toggle switch found on the VFG-1 knife, the box cutter configuration 50 may include a spring-loaded sliding/locking mechanism 51 to deploy a standard-sized industrial razor blade 50. The foregrip 30 can be disassembled and the position of the razor blade reversed to make use of the other half of the blade length. When both ends of the blade are completely dulled by excessive use, the end-user can easily replace the old blade with a fresh one.

Again, activation and usage are a one-handed operation, thus making the box cutter configuration as simple to use as the VFG-1 knife. And, too, replacement razor blades are easily acquired in large quantities at minimal expense.

In use, end-users simply press down on the spring-loaded slide lock 51 and push the button forward out the grip top 31 to deploy the razor blade. To retract, end-users again press down on the spring-loaded slide lock 51 and pull back on the button to withdraw the razor blade 50. The end-user again is provided a multi-functional tool that is both a foregrip and box cutter contained within the same unit, the foregrip providing a handle. This provides soldiers and others a useful edged-tool when deployed on field maneuvers and satisfies the need for one-handed operations. And, too, this makes the integral edged-tool available to those who otherwise would not be permitted to acquire the "gravity knife" configuration as described previously with the VFG-1 knife.

Figure 6:
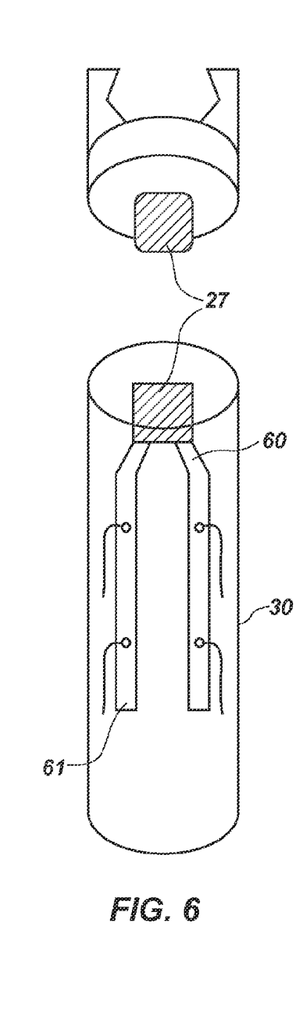
FIG. 6 is a diagrammed view of the vertical foregrip with multi-tool enclosed.

The VFG-3 (integral multi-tool configuration; FIG. 6) may be similar in design to the VFG-1 and VFG-2, wherein the body of the foregrip 30 attaches via a mounting device 25 to the Picatinny mounting rail 21. A multi-functional foregrip 30 that incorporates a unique multi-tool device 60 is provided. Contained within the interior 34 of the foregrip is the multi-tool device 60 that may be comprised of a "frame" or backbone 61 to which the various tools are attached.

The frame 61 may attach to the Picatinny mounting device 25 via a threaded knob 27 that is inserted into the mounting device 25 and screwed into place. When needed, the foregrip 30 may be removed as previously described, and the multi-tool 60 may be unscrewed from the Picatinny mounting device 25. Each of the tools mounted to the frame 61 may be folded away from the frame 61 on their individual hinge points for use. The various tools may range from commonly needed tools such as flat-tipped or Phillips-head screw drivers, small cutting blades, chisel points, or hex wrenches of various sizes, the types and mix of tools to be determined by the manufacturer, but the multi-tool device is intended to provide end-users with handily accessible tools without the need to carry a separate tool box. In use, the multi-tool device may be unscrewed from the Picatinny mounting device and the tools, which are folded along the body of the frame, may be rotated outward for use, then folded again and re-inserted into the body of the foregrip. Other prior art vertical foregrips do not generally use multi-tool devices.

Figure 7:
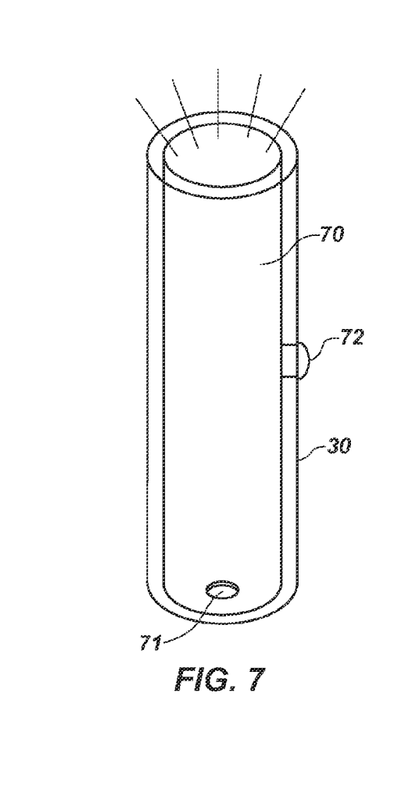
FIG. 7 is a diagrammed view of the vertical foregrip with spare flashlight.

The VFG-4 (integral spare flashlight; FIG. 7) may be similar in design to the VFG-1, VFG-2 and VFG-3 configurations (FIGS. 2-6), wherein the body of the foregrip 30 attaches via the mounting device 25 to the Picatinny mounting rail 21. While other manufacturers offer Picatinny rail-mounted flash or spotting lights, the present invention foregrip with integral flashlight 70 offers a handily accessible spare flashlight that does not require the end-user to remove components already mounted to their battle rifle. Often, Picatinny rail-mounted flashlights have external touch-pads to activate the flashlight when the end-user needs to deploy the light source in, say, clearing a room or when confronting a potential assailant. In that regard, the rail-mounted flashlight is more of a permanent component and part of the overall battle rifle configuration.

However, when a handy flashlight 70 is required, rather than remove a component from the battle rifle, soldiers (and other users) can quickly detach the present invention foregrip 30 with its internal spare flashlight 70 for those times when a quickly accessible light source is needed. In use, the spare flashlight contained within the vertical foregrip is removed by twisting and unlocking the foregrip threads/lugs similar to the previous configurations. The flashlight 70 within the foregrip 30 is activated, depending on manufacturing techniques, by a push-button 71 on the bottom of the flashlight 70 protruding through the foregrip bottom 32 or by a side-mounted on/off switch 72 protruding through a foregrip side 33, again depending on manufacturing techniques. The integral spare flashlight 70 provides an easily accessible light source that does not require the end-user to disassemble their rail-mounted flashlight, thereby compromising the setup of their battle rifle. The present invention VFG with spare flashlight provides a handy, readily available light source that is always available when needed.

Figure 8:
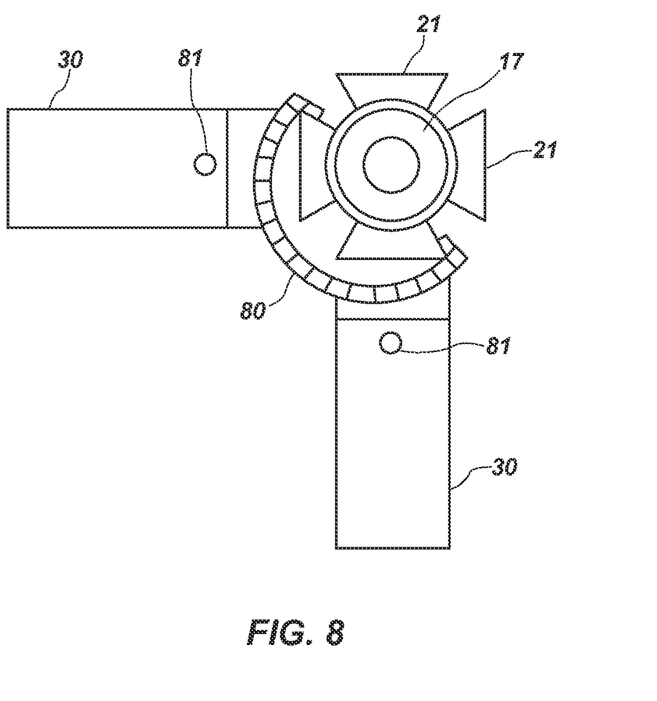
FIG. 8 is a diagrammed view of the vertical foregrip with a trunnion.

The VFG-5 (sliding/rotating mounting trunnion; FIG. 8) provides a trunnion 80 comprised of a half-round mounting device that attaches to a rail 21 in the Picatinny rail system 20 and allows for a full 180 degree movement of the VFG handle 30. For example, the VFG handle 30 may be positioned in either the six o'clock and nine o'clock positions (for right-handed shooters), the six o'clock and three o'clock positions (for left-handed shooters), or any position (i.e., angle) in between. The trunnion 80 may be manufactured in a manner that permits the unit to be reverse-mounted for either left- or right-handed shooters, but is essentially just one component. The vertical foregrip top 31 may be attached to the trunnion 80 in the same manner that other components are mounted to the Picatinny rail system 20, only the trunnion 80 is curved to permit movement by the vertical foregrip 30.

With the two components mounted together, i.e., trunnion 80 and rail 21, the vertical foregrip 30 would start in the normal six o'clock position. A release button 81 near the top 31 of the vertical foregrip releases the frictional grip on the trunnion 80 so the VFG 30 can be rotated upwards to the nine o'clock position. When the button 81 is released, the VFG 30 engages a notch in the trunnion to retain the VFG in the, now, horizontal position. When ready, end-users simply press the VFG release button 81 and return the foregrip to the six o'clock position. When the trunnion is mounted in reverse, the action of a left-handed shooter would be the same as for right-handed shooters, only the positions are six o'clock for the vertical deployment and three o'clock for the horizontal position. In use, grip positions can be changed from vertical to horizontal by depressing the release button built into the VFG and rotating the grip to either the nine o'clock or three o'clock positions, depending whether shooters are right- or left-handed.

Typical prior art vertical foregrips are just that, mounted in the vertical position. However, some modern tactical and firearms training courses advocate the "hand over foregrip" method of gripping the fore-end of the AR battle rifle to "drive" the weapon either left or right when the weapon is used in tactical situations. The ability to control how far the weapon swings when "driving the weapon" left or right means that shooters have more control over the weapon and can align on target faster without swinging too far in a given direction when moving from one position to another. The present invention VFG with trunnion mount 80 allows shooters to re-position their attached vertical foregrips 30 to virtually achieve the "hand over fore-end" type grip without having to release their hold on the rifle, while also being able to control the movement of the weapon just as securely and positively as if they were using the hand-over-fore-end grip method. Additionally, with the VFG able to move into either the nine o'clock or three o'clock positions, for shooters who are engaged in urban defense or house-clearing situations, the vertical foregrip can be moved to the horizontal position and the end of the foregrip can be placed against a door frame, thereby giving shooters a more stable platform from which to provide covering fire or engage an assailant. Being in the horizontal position and wedged against a door frame acts as a brace to stabilize the weapon to help achieve a more accurate sight-picture.

Figures 9, 10:
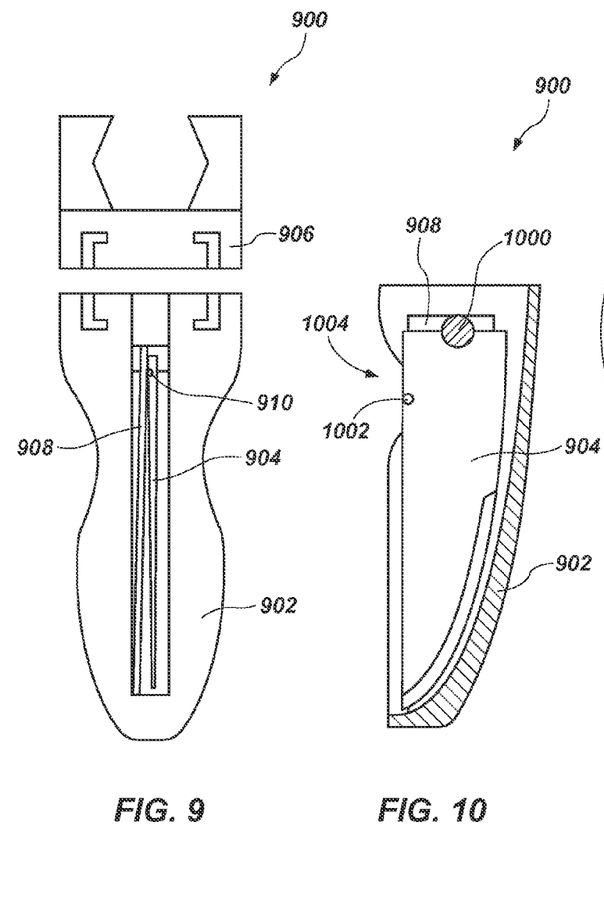
FIG. 9 is a front view of a vertical foregrip with a folding blade and liner-lock mechanism.
FIG. 10 is a partial section view of the vertical foregrip of FIG. 9.
Figure 11:
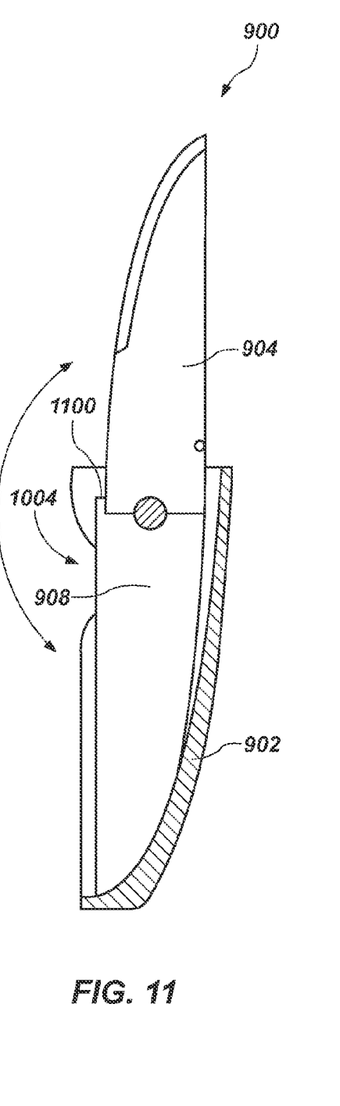
FIG. 11 is a partial section view of the vertical foregrip of FIG. 9 with the folding blade in an extended position.

Referring now to FIGS. 9-11, an embodiment of the VFG-6 (vertical foregrip with an integral folding blade that includes a liner-lock mechanism) is shown. A vertical foregrip 900 (FIG. 9) including a grip body 902 may be provided with an integral folding blade 904. The vertical foregrip 900 may be removably attached to a Picatinny rail 21 (FIG. 1) via a mounting device 906. The vertical foregrip 900 may include a liner-lock mechanism 908 disposed adjacent the folding blade 904 to lock the folding blade 904 in a deployed (e.g., extended) position relative to the grip body 902 and to prevent accidental closure of the folding blade 904 while the folding blade 904 is in use. The folding blade 904 may include a recess, e.g., a notch 910, formed on a lateral side of the folding blade 904 adjacent the liner lock 908.

FIG. 10 is a cross-sectional side view of the vertical foregrip 900 shown in FIG. 9. The folding blade 904 may be rotatably attached to the grip body 902 at a pivot 1000 such that while in a closed position, the folding blade 904 is substantially disposed within the grip body 902. The folding blade 904 may include a thumb-assist device, such as a thumb-screw 1002, to engage a firearm user's thumb to facilitate pushing the folding blade 904 such that the folding blade 904 pivots on the pivot 1000 into the deployed and locked position (FIG. 11). The liner-lock 908 may be made from a flexible material such as spring steel, and may be disposed within the grip body 902 adjacent the folding blade 904. The grip body 902 may include recessed portions 1004 on either side of the folding blade so that the user's thumb can engage the thumb-assist device 1002 to deploy the folding blade 904.

FIG. 11 is a cross-sectional view similar to the view of FIG. 10. In FIG. 11, the folding blade 904 is shown in a deployed and locked position. An edge 1100 of the liner-lock 908 may engage the notch 910 (FIG. 9) to prevent the folding blade 904 from closing. When the user desires to close the folding blade 904, the user may apply lateral pressure against a portion of the liner-lock 908 exposed through the recessed portions 1004 of the grip body 902 to disengage the edge 1100 of the liner-lock from the notch 910 in the folding blade 904 and enable the folding blade 904 to pivot to a closed (e.g., refracted) position (FIG. 10).

Figure 12:
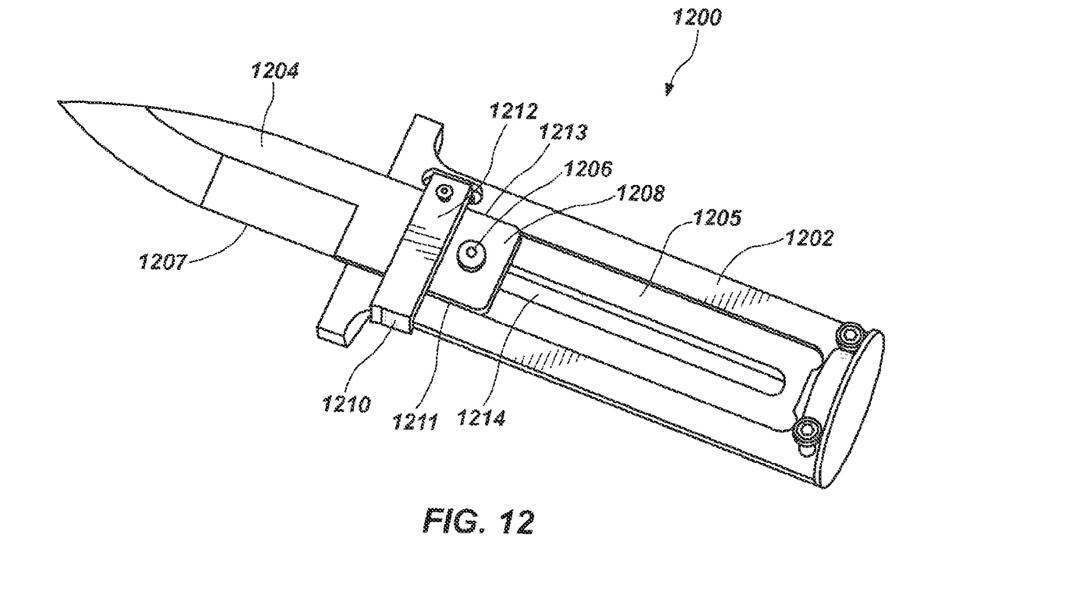
FIG. 12 is a partial section view of a vertical foregrip with an integral sliding blade.

Referring now to FIG. 12, another embodiment of the VFG-1 (vertical foregrip with an integral sliding blade) is shown in partial section. A vertical foregrip 1200 may include a grip body 1202 with a sliding blade 1204 disposed therein. The sliding blade 1204 may be configured to move between a fully refracted position, in which the sliding blade 1204 is fully enclosed within an internal blade cavity 1205 of the body 1202, to an extended position, in which a cutting edge 1207 of the sliding blade 1204 is substantially exposed beyond the grip body 1202, as shown in FIG. 12. The sliding blade 1204 may be precluded from moving from the refracted position when the grip body 1202 is attached to the mounting device 25 (FIGS. 2-4). The sliding blade 1204 may include a blade stop 1206, such as a pin, screw, tab, or flange protruding from a base portion 1208 of the sliding blade 1204. The blade stop 1206 may slide in a channel 1214 formed in the body 1202. A spring-loaded release button 1210 may include an elongated member 1212 extending into the grip body 1202 generally perpendicular to the length of the sliding blade 1204. The elongated member 1212 may extend from a first lateral edge 1211 of the sliding blade 1204 to a second lateral edge 1213 opposite the first lateral edge 1211. When the sliding blade 1204 is in an extended position, as shown in FIG. 12, the blade stop 1206 may abut the elongated member 1212 of the release button 1210 to prevent the sliding blade 1204 from sliding clear of (i.e., completely exiting) the grip body 1202.

Figure 13:
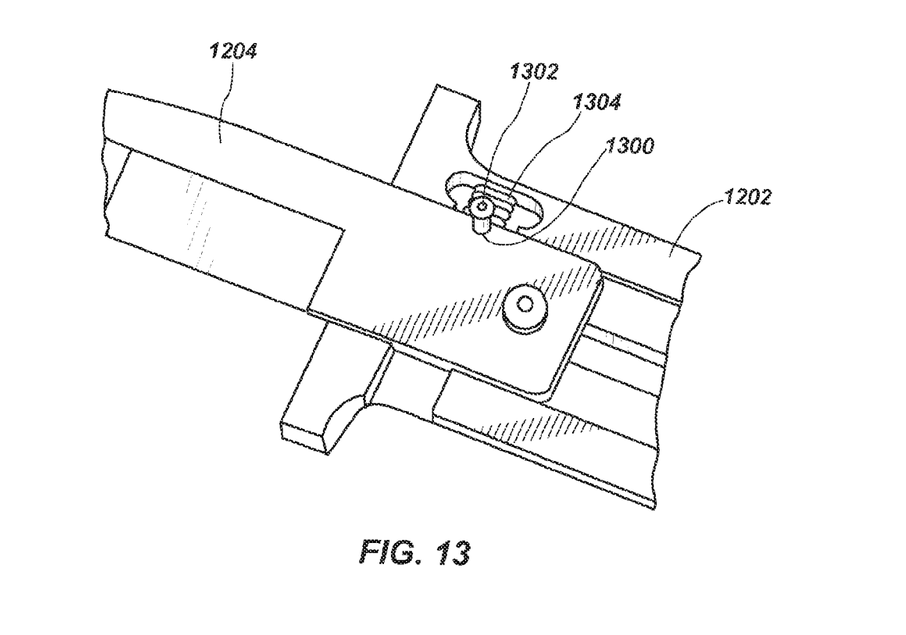
FIG. 13 is an enlarged partial section view of the vertical foregrip of FIG. 12.

FIG. 13 shows an enlarged view of the vertical foregrip of FIG. 12, with the spring-loaded release button 1210 shown in FIG. 12 omitted from the view of FIG. 13 to show additional features. The sliding blade 1204 may include a recessed area, e.g., a notch 1300, formed in the second lateral edge 1213 of the sliding blade 1204. A locking element such as a locking pin 1302 may be biased toward the notch 1300 by a biasing element, such as a spring 1304, disposed between a portion of the grip body 1202 and the locking pin 1302. When the sliding blade 1204 is urged from a refracted position within the grip body 1202 to an extended position by, for example, gravity, or centrifugal force resulting from a movement of the user, such as a "flick" of the user's wrist, the spring 1304 may urge the locking pin 1302 into the notch 1300 to lock the sliding blade 1204 in a deployed position.

When the user desires to return the sliding blade 1204 to a retracted position, the user may depress the release button 1210 (FIG. 12) and the elongated member 1212 (FIG. 12) of the release button may bear against the locking pin 1302 (FIG. 13), moving the locking pin 1302 against the biasing force of the spring 1304 and out of the notch 1300. The sliding blade 1204 may then be free to drop back into the grip body 1202 of the vertical foregrip 1200 to return to a retracted position.

In summary, the present invention VFG configurations present shooters with options and tools not previously available in the firearms industry. This versatility helps end-users (whether soldiers, police officers, or civilians) to select the multi-functional tool that best suits their mission, surroundings, or personal needs.

Additional non-limiting example embodiments of the disclosure are set forth below.

Embodiment 1

A foregrip for a firearm, comprising: a mounting device configured to attach to a mounting rail of a firearm; a grip body with a top portion configured to be removably attached to the mounting device and a lateral side portion configured to be gripped by the hand of a person using a firearm; a cavity disposed within the grip body; and a blade disposed at least partially within the cavity, wherein the blade is movable between a refracted position and a deployed position relative to the grip body.

Embodiment 2

The foregrip of Embodiment 1, wherein the blade is moveable along a direction substantially parallel to a length of the grip body.

Embodiment 3

The foregrip of Embodiment 2, wherein the blade moves out from the cavity within the grip body through an opening in the top portion of the grip body as the blade moves from the refracted position to the deployed position relative to the grip body.

Embodiment 4

The foregrip of Embodiments 2 or 3, wherein the blade is precluded from moving from the refracted position to the deployed position relative to the grip body when the grip body is attached to the mounting device.

Embodiment 5

The foregrip of any one of Embodiments 1 through 4, wherein the grip body further comprises a locking mechanism configured to lock the blade in the deployed position.

Embodiment 6

The foregrip of Embodiment 5, wherein the locking mechanism is further configured to lock the blade in the refracted position.

Embodiment 7

The foregrip of Embodiments 5 or 6, wherein the blade has a recess on an outer surface of the blade, and wherein the locking mechanism includes at least one movable locking feature configured to engage the at least one recess in the blade to preclude relative movement between the blade and the grip body when the at least one movable locking feature is engaged with the at least one recess in the blade.

Embodiment 8

The foregrip of Embodiment 7, wherein the locking mechanism further comprises a release button on an exterior of the grip body and coupled with the movable locking feature, such that depressing the release button disengages the movable locking feature from the at least one recess in the blade to allow relative movement between the blade and the grip body.

Embodiment 9

The foregrip of any one of Embodiments 1 through 8, wherein the blade is configured to drop from the retracted position to a deployed position by gravity when the firearm user holds the grip body with the top portion facing generally downward.

Embodiment 10

The foregrip of any one of Embodiments 1 through 9, wherein the mounting device is configured for attachment to a Picatinny rail.

Embodiment 11

The foregrip of any one of Embodiments 1 through 10, wherein the mounting device and the grip body include complementary interlocking features that may be engaged with one another to attach the grip body to the mounting device, and that may be disengaged from one another to remove the grip body from the mounting device.

Embodiment 12

The foregrip of Embodiment 11, wherein mechanical interference between the complementary interlocking features of the grip body and the mounting device secures the grip body to the mounting device when the complementary interlocking features are engaged with one another.

Embodiment 13

The foregrip of Embodiment 12, wherein the complementary interlocking features of the grip body and the mounting device are engaged with one another by abutting the grip body against the mounting device and rotating the grip body relative to the mounting device.

Embodiment 14

The foregrip of Embodiment 13, wherein the complementary interlocking features of the grip body and the mounting device are engaged with one another by abutting the grip body against the mounting device and rotating the grip body relative to the mounting device about a longitudinal axis of the grip body.

Embodiment 15

The foregrip of any one of Embodiments 1 through 14, wherein the blade is affixed to a frame removable from the grip body, the frame including at least one additional tool.

Embodiment 16

A method of manufacturing a foregrip for a firearm, comprising: forming a mounting device configured to mount to a mounting rail of a firearm; forming a grip body including a top portion configured to removably attach to the mounting device and a lateral side portion configured to be gripped by a firearm user; and providing a blade disposed within a cavity of the grip body, wherein the blade is moveable between a refracted and a deployed position.

Embodiment 17

A method of using a firearm, comprising: coupling a mounting device to a rail of the firearm; removably attaching a foregrip including a utility device therein to the mounting device, the foregrip including a grip body having a top portion configured for attachment to the mounting device, a lateral side portion configured to be gripped by a firearm user, and a blade disposed within a cavity of the grip body, the blade being moveable between a retracted position and a deployed position relative to the grip body; detaching the foregrip from the mounting device and the firearm; and moving the blade from the retracted position to the deployed position.

Embodiment 18

A foregrip for a firearm, comprising: a mounting device configured to attach to a mounting rail of a firearm; a grip body with a top portion configured to be removably attached to the mounting device and a lateral side portion configured to be gripped by the hand of a person using a firearm; a cavity disposed within the grip body; and a utility device disposed at least partially within the cavity.

Embodiment 19

The foregrip of Embodiment 18, wherein the utility device is configured to be at least partially removed out from the cavity within the grip body through an opening in the top portion of the grip body, and wherein the utility device is precluded from being at least partially removed out from the cavity within the grip body when the grip body is attached to the mounting device.

Embodiment 20

The foregrip of Embodiments 18 or 19, wherein the utility device comprises at least one of a blade, a light, and a multi-tool.

The example embodiments of the disclosure described above do not limit the scope of the invention, since these embodiments are merely examples of embodiments of the invention, which is defined by the scope of the appended claims and their legal equivalents. Any equivalent embodiments are intended to be within the scope of this invention. Indeed, various modifications of the disclosure, in addition to those shown and described herein, such as alternate useful combinations of the elements described, will become apparent to those skilled in the art from the description. Such modifications and embodiments are also intended to fall within the scope of the appended claims.

What is claimed is:

1. A foregrip for a firearm, comprising: a mounting device configured to attach to a mounting rail of a firearm; a grip body with a top portion configured to be removably attached to the mounting device and a lateral side portion configured to be gripped by the hand of a person using a firearm; a cavity disposed within the grip body; and a blade disposed at least partially within the cavity, wherein the blade is movable between a retracted position and a deployed position relative to the grip body;
wherein the grip body further comprises a locking mechanism configured to lock the blade in the deployed position; and
wherein the blade defines at least one recess, and wherein the locking mechanism includes at least one movable locking feature configured to engage the at least one recess to preclude relative movement between the blade and the grip body when the at least one movable locking feature is engaged with the at least one recess.

2. The foregrip of claim 1, wherein the blade is moveable along a direction substantially parallel to a length of the grip body.

3. The foregrip of claim 2, wherein the blade moves out from the cavity within the grip body through an opening in the top portion of the grip body as the blade moves from the retracted position to the deployed position relative to the grip body.

4. The foregrip of claim 2, wherein the blade is precluded from moving from the retracted position to the deployed position relative to the grip body when the grip body is attached to the mounting device.

5. The foregrip of claim 1, wherein the locking mechanism is further configured to lock the blade in the retracted position.

6. The foregrip of claim 1, wherein the locking mechanism further comprises a release button on an exterior of the grip body and coupled with the movable locking feature, such that depressing the release button disengages the movable locking feature from the at least one recess in the blade to allow relative movement between the blade and the grip body.

7. The foregrip of claim 1, wherein the blade is configured to drop from the refracted position to a deployed position by gravity when the firearm user holds the grip body with the top portion facing generally downward.

8. The foregrip of claim 1, wherein the mounting device is configured for attachment to a Picatinny rail.

9. The foregrip of claim 1, wherein the mounting device and the grip body include complementary interlocking features that may be engaged with one another to attach the grip body to the mounting device, and that may be disengaged from one another to remove the grip body from the mounting device.

10. The foregrip of claim 9, wherein mechanical interference between the complementary interlocking features of the grip body and the mounting device secures the grip body to the mounting device when the complementary interlocking features are engaged with one another.

11. The foregrip of claim 10, wherein the complementary interlocking features of the grip body and the mounting device are engaged with one another by abutting the grip body against the mounting device and rotating the grip body relative to the mounting device.

12. The foregrip of claim 11, wherein the complementary interlocking features of the grip body and the mounting device are engaged with one another by abutting the grip body against the mounting device and rotating the grip body relative to the mounting device about a longitudinal axis of the grip body.

13. The foregrip of claim 1, wherein the blade is affixed to a frame removable from the grip body, the frame including at least one additional tool.

14. A method of manufacturing a foregrip for a firearm, comprising: forming a mounting device configured to mount to a mounting rail of a firearm; forming a grip body including a top portion configured to removably attach to the mounting device and a lateral side portion configured to be gripped by a firearm user; and providing a blade disposed within a cavity of the grip body, wherein the blade is moveable between a refracted and a deployed position, wherein the grip body further comprises a locking mechanism configured to lock the blade in the deployed position; and wherein the blade defines at least one recess, and wherein the locking mechanism includes at least one movable locking feature configured to engage the at least one recess to preclude relative movement between the blade and the grip body when the at least one movable locking feature is engaged with the at least one recess.

15. A method of using a firearm, comprising: coupling a mounting device to a rail of the firearm; removably attaching a foregrip including a utility device therein to the mounting device, the foregrip including a grip body having a top portion configured for attachment to the mounting device, a lateral side portion configured to be gripped by a firearm user, and a blade disposed within a cavity of the grip body, the blade being moveable between a refracted position and a deployed position relative to the grip body; detaching the foregrip from the mounting device and the firearm; and moving the blade from the retracted position to the deployed position; and locking the blade in the deployed position wherein the grip body further comprises a locking mechanism configured to lock the blade in the deployed position; and wherein the blade defines at least one recess, and wherein the locking mechanism includes at least one movable locking feature configured to engage the at least one recess to preclude relative movement between the blade and the grip body when the at least one movable locking feature is engaged with the at least one recess.

16. A foregrip for a firearm, comprising: a mounting device configured to attach to a mounting rail of a firearm; a grip body with a top portion configured to be removably attached to the mounting device and a lateral side portion configured to be gripped by the hand of a person using a firearm; a cavity disposed within the grip body; and a utility device disposed at least partially within the cavity, wherein the grip body further comprises a locking mechanism configured to lock the utility device in the deployed position; and wherein the utility device defines at least one recess, and wherein the locking mechanism includes at least one movable locking feature configured to engage the at least one recess to preclude relative movement between the utility device and the grip body when the at least one movable locking feature is engaged with the at least one recess.

17. The foregrip of claim 16, wherein the utility device is configured to be at least partially removed out from the cavity within the grip body through an opening in the top portion of the grip body, and wherein the utility device is precluded from being at least partially removed out from the cavity within the grip body when the grip body is attached to the mounting device.

18. The foregrip of claim 16, wherein the utility device comprises at least one of a blade, a light, and a multi-tool.

19. A foregrip for a firearm, comprising: a mounting device configured to attach to a mounting rail of a firearm; a grip body with a top portion configured to be removably attached to the mounting device and a lateral side portion configured to be gripped by the hand of a person using a firearm; a cavity disposed within the grip body; and a blade disposed at least partially within the cavity, wherein the blade is movable between a retracted position and a deployed position relative to the grip body;

wherein the mounting device and the grip body include complementary interlocking features that may be engaged with one another to attach the grip body to the mounting device, and that may be disengaged from one another to remove the grip body from the mounting device;

wherein mechanical interference between the complementary interlocking features of the grip body and the mounting device secures the grip body to the mounting device when the complementary interlocking features are engaged with one another; and wherein the complementary interlocking features of the grip body and the mounting device are engaged with one another by abutting the grip body against the mounting device and rotating the grip body relative to the mounting device.

* * * * *

UNITED STATES PATENT AND TRADEMARK OFFICE
CERTIFICATE OF CORRECTION

PATENT NO. : 9,228,796 B2  
APPLICATION NO. : 14/143987  
DATED : January 5, 2016  
INVENTOR(S) : Adcock, Jr. et al.

Page 1 of 1

It is certified that error appears in the above-identified patent and that said Letters Patent is hereby corrected as shown below:

Claims

Column 14, line 40 (Claim 15) change "a refracted position" to --a retracted position--

Signed and Sealed this
Twenty-ninth Day of March, 2016

Michelle K. Lee
*Director of the United States Patent and Trademark Office*